(12) United States Patent
Parris (10) Patent No.: US 11,534,945 B2
(45) Date of Patent: Dec. 27, 2022

(54) BRAGG-PEAK THREE-DIMENSIONAL MANUFACTURING WITH RESINS

(71) Applicant: George Edward Parris, Gaithersburg, MD (US)

(72) Inventor: George Edward Parris, Gaithersburg, MD (US)

(73) Assignee: Directed Energy Materials LLC, Woodbridge, VA (US)

( * ) Notice: Subject to any disclaimer, the term of this patent is extended or adjusted under 35 U.S.C. 154(b) by 0 days.

(21) Appl. No.: 16/350,502

(22) Filed: Nov. 26, 2018

(65) Prior Publication Data
US 2021/0170639 A1    Jun. 10, 2021

(51) Int. Cl.
| | | |
|---|---|---|
| *B29C 64/264* | (2017.01) | |
| *B29C 64/135* | (2017.01) | |
| *B29C 64/165* | (2017.01) | |
| *B33Y 10/00* | (2015.01) | |
| *B29K 105/20* | (2006.01) | |
| *B29K 105/06* | (2006.01) | |
| *A61N 5/10* | (2006.01) | |
| *B33Y 40/20* | (2020.01) | |
| *B29C 35/08* | (2006.01) | |
| *B29C 35/00* | (2006.01) | |
| *B29L 31/00* | (2006.01) | |
| *B33Y 40/00* | (2020.01) | |

(52) U.S. Cl.
CPC ............ *B29C 35/0866* (2013.01); *A61N 5/10* (2013.01); *B29C 35/002* (2013.01); *B29C 64/135* (2017.08); *B29C 64/165* (2017.08); *B29C 64/264* (2017.08); *B33Y 40/20* (2020.01); *A61N 2005/1087* (2013.01); *B29C 2035/0872* (2013.01); *B29K 2105/06* (2013.01); *B29K 2105/20* (2013.01); *B29L 2031/7532* (2013.01); *B33Y 10/00* (2014.12); *B33Y 40/00* (2014.12)

(58) Field of Classification Search
CPC ........ B29C 35/0866; B29C 2035/0872; B29K 2105/06; B29K 2105/20
See application file for complete search history.

(56) References Cited

U.S. PATENT DOCUMENTS

| | | | | |
|---|---|---|---|---|
| 6,569,602 | B1 * | 5/2003 | Wang | G03F 7/027 |
| | | | | 430/281.1 |
| 9,498,920 | B2 * | 11/2016 | DeSimone | B29C 64/40 |
| 2006/0292709 | A1 * | 12/2006 | Hoshino | C23C 16/047 |
| | | | | 438/14 |
| 2015/0258734 | A1 * | 9/2015 | Okamoto | B29C 64/112 |
| | | | | 235/488 |
| 2020/0164572 | A1 * | 5/2020 | Bartow | G03F 7/038 |
| 2021/0220948 | A1 * | 7/2021 | Sekiguchi | B23K 26/08 |

FOREIGN PATENT DOCUMENTS

WO    WO-2011082152 A1 *    7/2011    ......... A61B 17/7208

* cited by examiner

*Primary Examiner* — Xiao S Zhao
*Assistant Examiner* — John J DeRusso
(74) *Attorney, Agent, or Firm* — Ingenium Patents LLC; Peter R. Kramer (57) ABSTRACT

This patent application claims the use of directed energy in the form of electronically scanned ion beams to form plastic parts by selectively curing commodity or engineering resin in the shape of the part. Polymerization is limited to the vicinity of the controlled Bragg-peak of the ion beam (i.e., where linear energy transfer is maximized), if necessary, by the use of chemical polymerization inhibitors or conditions that inhibit polymerization.

15 Claims, 5 Drawing Sheets

BRAGG-PEAK THREE-DIMENSIONAL MANUFACTURING WITH RESINS

FIELD OF THE INVENTION

This invention is in the general area of manufacturing plastic products from organic resins. It is similar to three-dimensional printing, but instead of building up a structure by step-wise or continuously adding two-dimensional layers, this invention envisions building a three-dimensional part inside a resin (e.g., a viscous liquid or solid without support or a fluid liquid with pre-positioned supporting structures) through an application of ion beam technology such as currently used to treat cancer (e.g., proton beam therapy). This invention uses the unique properties of ion beams to deposit most of their energy at a position known as the "Bragg peak," to initiate polymerization in a small selected volume of space (i.e., a 3-D pixel). These pixels combine to form the new plastic part, which may incorporate prefabricated and pre-positioned sub-parts.

BACKGROUND OF THE INVENTION

Prior Art

Currently, three-dimensional plastic parts are typically extruded, cast or machined. Within the last decade, the use of printing technology to build up three-dimensional parts from two-dimensional layers (known as "three-dimensional printing") has become popular because it offers some flexibility in design and manufacturing, although it is inherently slow because one layer is built as a time. Typically, these printing techniques are used to cure polymer resins. Most commercial resins are cured by UV radiation that induces free radical curing of acrylic compounds (acrylates). Free radical curing systems are readily inhibited by free radical scavengers such as oxygen. Initiation of UV-curing is limited to a shallow depth depending on the absorption and transmission of photons (electromagnetic radiation) by the resin. This factor means that UV curing is normally not efficient for deeper layers of mixtures including opaque solids. Carbon® (Redwood, Calif.) has used these properties to develop a method for continuous liquid interface production (U.S. Pat. No. 9,498,920 B2 CLIP™) and other practitioners have developed less efficient step-wise technologies to create two-dimensional slices of objects that are layered into a three-dimensional part. These technologies are inherently slow (layer-by-layer) and require a moving stage upon which the plastic part is built and are not compatible with the use of solid fillers or reinforcing fibers within the resin.

This Invention

I am here disclosing a true "three-dimensional manufacturing" technique, which has much more flexibility than three-dimensional printing. It may also be much faster than 3-D printing because the product is not made up sequentially layer-by-layer. Moreover, the surface shape can be quickly defined and established; followed by curing the interior resin by mass heating after the defined part is removed from the excess resin.

In contrast to electromagnetic photons (UV), accelerated particles (ions) interact with matter in an entirely different way. In 1903, Sir William Henry Bragg (1862-1942) discovered that the linear-energy-transfer (LET, i.e., energy transferred to the medium by an ion passing through a medium, J/meter) increases as the velocity of the particle decreases. LET of charged particles entering a medium is inversely proportional to the square of their velocity. Thus, LET dramatically increases as the velocity of the particle approaches zero. Unlike photons of electromagnetic radiation, which dissipate their energy progressively as they pass through a medium, the energy of an ion beam is primarily dissipated at a predictable, controllable and reproducible depth within the medium (a.k.a., the Bragg peak) [FIG. 1]. The Bragg peak, for an individual particle or stream of particles can be viewed as a three-dimensional pixel of high energy. This energy causes local heating and formation of free radicals and ions. Thus, the chemical curing mechanism of UV-curing and Bragg-peak-curing is virtually the same; the difference is how the energy is delivered. This is a specific example of "directed energy" manufacturing, which was the subject of my original (parent) patent application. (This specific application was mentioned on page 15 lines 26-29 of the patent application Ser. No. 15/927,407 filed Mar. 21, 2018 based on a previous provisional filing 62/547, 963 Aug. 21, 2017.)

To my knowledge, the idea of using Bragg-peak energy to initiate curing of resins is unique and disclosed for the first time in my earlier patent application (Ser. No. 15/927,407 filed Mar. 21, 2018) and elaborated on here. The ion beam technique has been the subject of extensive development because the reactive chemical species (i.e., radicals and ions) initiate chemical chain reactions that can be lethal to biological cells. This technology (e.g., proton therapy) has now reached a high level of refinement and control and is being routinely used to treat cancer patients in lieu of surgery or x-ray. The particle beam is used to create a three-dimensional pattern of reacting pixels within tumors of complex shapes that are often surrounded by important healthy tissues that must not be damaged.

Because the main interaction of the high-energy ions with media is to release a dense field of free radicals and ions in the Bragg-peak, it is possible to use this phenomenon to initiate polymerization in monomers and resins of organic compounds ("resins" are partially polymerized monomers with various additives). The key element of this invention is the uses of the well-established ion beam technology to initiate polymerization/curing/crosslinking of fluid resins (or finely divided solid resins) to form a mechanical part inside a solid or viscous liquid medium or a fluid medium that includes pre-positioned solid supports/fillers/reinforcing materials to which the partially cured plastic can adhere.

The chemistry of curing the resin is essentially the same as when using heat or UV light and the unique feature is using the ion beam technology to accurately initiate curing at spots (pixels) deep within the reaction mixture (i.e., not limited to the surface of the reaction mixture). This feature allows the introduction of inert solids into the reaction mixture [FIGS. 2 and 3]. In comparison, it is not possible (or at least very inconvenient) to introduce ridged solid items into the resin when used in continuous or step-wise three-dimensional printing technologies because in the printing technologies the stage upon which the part is built must move in some way. This n feature of ion beam manufacturing claimed here allows the introduction of reinforcing lattices and modifications of the bulk properties of the finished plastic.

Another major potential advantage of ion beam manufacturing is the fact that all printing technologies must work layer-by-layer with mechanical motion and necessarily will require a long time to build the part. In the case of ion beam manufacturing, multiple beams can work simultaneously

[FIGS. 2, 3, 4 and 5] and the beams are scanned electronically to create the layers of pixels that form the final product. The several beams can originate from different directions and follow different paths to the Bragg peak(s) [FIG. 2]. Moreover, the Bragg pixels can be formed in any order, not just line-by-line or layer-by-layer adjacent to a stage [FIGS. 2, 3, 4 and 5]. For example, the shape of a part can be quickly established by scanning its surface, without taking the time to cure all the volume within the surface using the ion beam. The outlined part (with uncured resin inside) can be separated from the excess resin and the interior of the partially finished part can then be completely cured by heat or any other curing technology independent of the ion beam [FIG. 4].

Although the cost of building and operating an ion beam facility is quite high, the enhanced speed and flexibility of production and the possibility of collocating manufacturing and medical treatment facilities could greatly improve the economics. In particular, at this time, ion beam therapy is restricted to the most serious medical emergencies (inoperable tumors) because of cost and is only available at a few medical centers. But, if the cost were lower, it might prove desirable and feasible to apply ion beams to treat other medical issues such as localized infections (e.g., antibiotic resistant tuberculosis, abscesses or cysts), operable tumors, malformations (ingrown toenails) or even cosmetic issues (acne).

BRIEF DESCRIPTION OF THE DRAWINGS

FIG. 1. This figure demonstrates the principle of Bragg peak activation of resin curing. A particle beam [2] enters a resin mixture [1] and initiates effective curing (polymerization) only at the Bragg peak (i.e., Bragg pixel) [3] where the LET density exceeds the threshold set by suppressing agents and conditions [4]. The concept is illustrated in the graph at the top which shows the typical profile of linear energy transfer (LET) [5] and the threshold for initiation of effective curing (polymerization) [6].

FIG. 4. This embodiment shows ion beams from two independent sources [7] building a part [12] on a stage [14]. The approach used here saves time by producing the "skin" of the part while leaving the core of the part as uncured resin [13]. The part will be removed from excess resin and curing of the core and skin will be completed using general heating or some other method of directed energy.

DETAIL DESCRIPTION OF THE INVENTION

The generation and application of ion beams is not within the scope of this invention; it is regarded as a well-developed tool (invented and developed for a different application) that can be adapted to produce protons or other ions of interest, accelerate the ions to very high velocities and guide them into a reaction mixture. It is also known that the depth of penetration of an ion beam into a target (i.e., a human being) or condensed phase (liquid or solid) can be calculated and adjusted by changing the velocity of the ions, or adding high-density or condensed phase shielding to the exterior of the target. The ion beam can be finely adjusted by electromagnetic effects on the beam and gross adjustments can be made by reorienting the target or the beam. Finally, the current electron beam technology includes the ability to quickly scan the beam and adjust the depth of penetration and to program exactly how much energy (actually "energy density" typically measured in Grays, 1 G=1 J/kg) will be delivered into a specifically defined three-dimensional volume (i.e., pixel). This tool is currently being used to selectively kill tumors in human beings while sparing adjacent healthy tissues.

Figure 1:
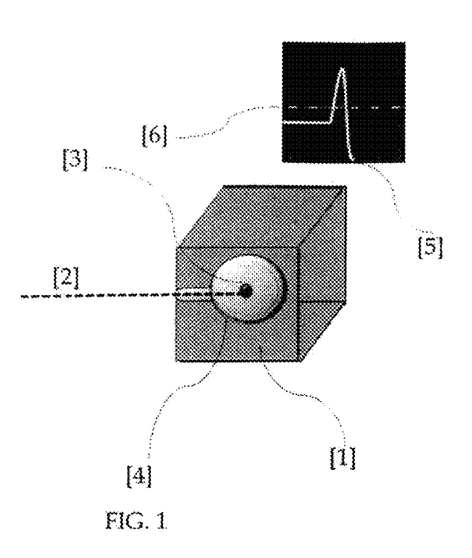
Figure 2:
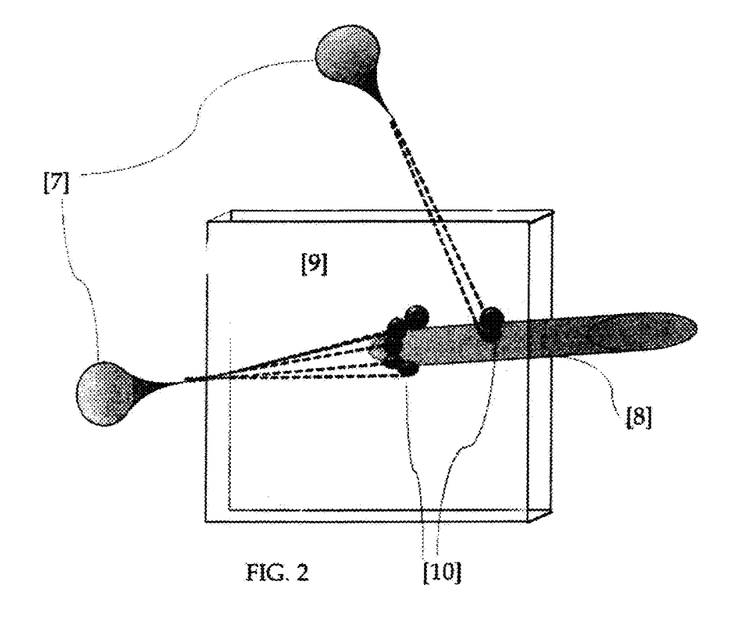
FIG. 2. This embodiment show use of simultaneously applied ion beams from two sources [7] to fabricate a part [10] in contact with an inert part [8] introduced into the reaction medium [9]. The beams are being scanned independently from different directions to produce Bragg pixels [10] of preselected size of curing resin in a preselected order. This demonstrates the speed and flexibility of this form of "directed energy Three-Dimensional Manufacturing" relative to e.g., continuous liquid interface production (CLIP), casting, milling or extruding.
Figure 3:
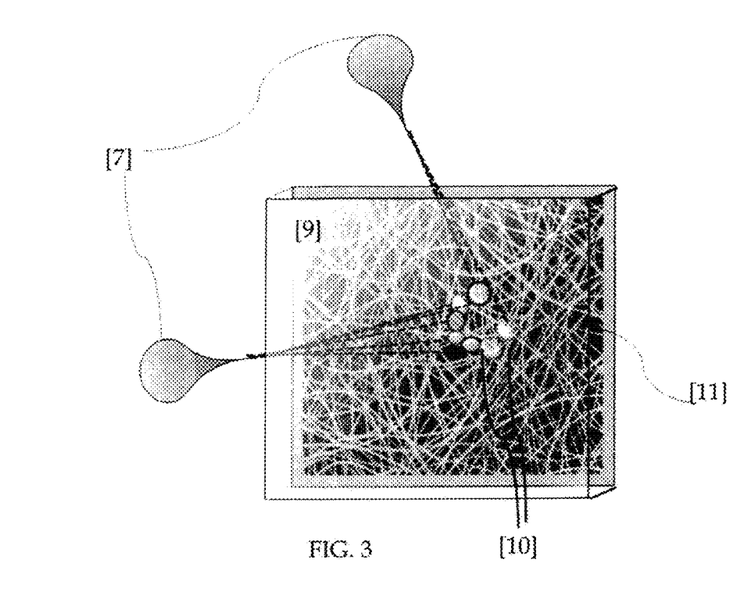
FIG. 3. This embodiment shows ion beams from two independent sources [7] building a part [10] within a mesh [11] of (reinforcing) fibers in the reaction mixture [9]. Once, the resin is removed from the excess resin and completely cured, the unwanted fibers can be trimmed.
Figure 4:
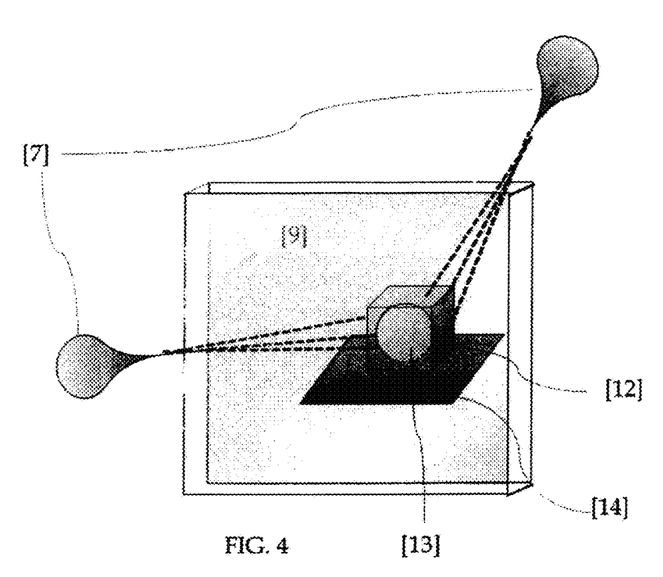

Here we will only refer to the "ion beam" [2 in FIG. 1] with the understanding that it can be rapidly adjusted and scanned [7 in FIG. 2] according to a pre-determined program to deliver a selected energy density (J/kg) into a pre-determined volume of virtually any shape inside a "reaction medium." The Bragg peak (i.e., the point of maximum delivered energy density) [3 in FIG. 1] is scanned in three dimensions and each ion (or ion cluster) impact results in what we call a "three-dimensional pixel" [10 in FIG. 2 or 3] where free radical density is created and can initiate a polymerization chain reaction, which radiates outward. The rate and effective distance of spread of the free radical reaction (i.e., curing the resin) is limited by the presence of compounds (inhibitors) that terminate the chain reaction or conditions (e.g., temperature) that suppress the propagation rate. Thus, the size of the three-dimensional pixel of cured resin can be controlled. If the three-dimensional pixels are close enough to overlap, effective macroscopic curing of resins occurs. If these pixels are widely dispersed or very small, effective curing of a resin does not occur.

The invention of interest here is the application of particle beams to curing resins to manufacture products. The chemistry is not significantly different from the chemistry of resin curing using UV light. What is novel and original is the use of proton beams to selectively polymerize/cure the resins in a three-dimensional pattern deep within the resin reaction mixture [FIG. 1, 2, or 3]. This pattern can be completely independent of a working surface, it can take on any shape, it can be formed in any sequence, it can be formed around inert inclusions [FIGS. 2 and 3], and it can be formed using multiple ions beams currently [FIGS. 2 and 3]. Moreover, ions beams can arrive at the same spot (Bragg peak) from different directions; thus, minimizing the energy density delivered to regions of the reaction mixture that are not intended for curing. This inventive method can be performed while concurrently applying other forms of energy (directed or undirected) to the resin/reaction mixture to facilitate formation/curing of the product.

Of course, the equipment needed to establish a manufacturing facility (including an ion accelerator and a complex computer-controlled beam director and target stage) is very expensive. Nonetheless, commercial applications have been introduced at a number of sites for treatment of tumors in humans. The unit cost of these treatments is very high and the market is currently relatively small. Moreover, the treatment of tumors in humans requires that the tumor (which is out of the control of the operator) be located, mapped and positioned appropriately for targeting with the ion beam. These requirements are much more stringent than envisioned for manufacturing. In manufacturing, the operator will determine the shape of the object to be manufactured and can make use of well-known geometrical shapes in developing the scanning program(s). Nonetheless, the techniques that have been developed to map tumors, might be useful to scan existing objects and develop a program for manufacturing identical objects using the methodology claimed here.

Instead of treating one unique tumor, a manufacturing process will typically produce thousands of each object. Thus, the process can be highly automated driving down the unit cost. In addition, production runs can be interrupted to make "one-off" special order (e.g., prototype) parts simply by replacing one program with another (i.e., no retooling necessary). Thus, we believe that the use of the ion beam for manufacturing will be fast, allow unique manufacturing options and produce high quality products cost-competitively with three-dimensional printing technologies or other manufacturing techniques. Moreover, by co-locating manufacturing and medical (e.g., proton therapy) facilities, key elements can be shared (e.g., the ion accelerator) and the cost of proton therapy for cancer will go down significantly, while it is made more available to the patients that need it. In particular, it may prove economical to extend proton therapy to treatment of localized infections, which are not amenable to drug therapy (including antibiotic resistant tuberculosis nodules in the lungs, abscesses and cysts). There are likely other applications that a currently not economically available in medicine and other manufacturing, chemical or metallurgical applications.

EXAMPLES

Example 1. A viscous polymer resin (commodity or engineering) is placed in a temperature-controlled container and mounted in an ion beam device (similar to that used in proton therapy for cancer). The ion beam controls have been programmed to produce a three-dimensional image of a standard part [FIGS. 2 and 3]. The beam(s) is turned on and the part is produced in the viscous resin. The resin is warmed or diluted with solvent to make it mobile and the part is gently extracted from the resin. Curing is completed by exposure of the partially cured object to heat or other energy sources. The excess resin is recycled into the process. The entire process is automated to robotically operate around and interface with the ion beam equipment.

Example 2. The system operates as in Example 1, except the resin is prepared with dispersed inert particles that are to be encapsulated in the final product. These particles might be small pieces of metal, glass, ceramics, polymers, fibers [11 in FIG. 3], foams, biodegradable materials or pigments, which are intended to modify the bulk properties of the final material (e.g., color, conductivity, flexibility, hardness, finish, density, biodegradability etc.).

Example 3. The system operates as in Example 1, but the reaction vessel can be sealed and pressurized. The resin is placed under vacuum to remove any gases (air) and then it is pressurized with the pure gases of interest (e.g., oxygen). To enhance the bulk concentration of gas (e.g., oxygen) small porous inert particles (e.g., molecular sieve, wood fiber) may be pressurized and incorporated into the resin. The pressure and gas can be varied to introduce a variety of bulk properties in the final product. In the case of oxygen, the gas may be used to limit the growth of cured pixels of the resin. A liquid or gas may be injected into the reaction mixture to form one or more bubbles within the resin before, during, or after application of the ion beam.

Example 4. The system is operated as in Example 1, but one or more (large) items made of inert materials are placed in predetermined arrays in the reaction vessel [8 in FIG. 2]. These items might be parts (made of metals, plastics, carbon fiber etc.) that are to be partially or totally encapsulated by or chained to the finished plastic product. The items may become integral parts of the final product by bonding with the resin; or they may be used as forms around which the resin is cured. They, may or may not be intended to help support the resin as it cures. These preformed and prepositioned items contribute to the final shape, hardness, rigidity, conductivity, etc. of the part and may be intended to provide specific features in a complex part such as passageways for light, fluids or electrical conductors. They could also provide heavy-duty mounting accessories for the part (e.g., a metal mounting bracket build into a plastic part) or a special metallic covering for part or all of the part (e.g., for thermal insulation or chemical resistance). After curing the resin, any excess projecting fibers etc. can be trimmed mechanically. The compatibility of this process with solid additives in the resin is one of the features that cannot easily be accomplished with step-wise or continuous three-dimensional printing techniques. Incorporation of inert materials in the resin is also desirable because it might allow a commodity plastic to acquire properties (e.g. strength, rigidity) similar to an engineering plastic.

Example 5. To expedite any of the processes in examples 1-4, multiple independent ion beams can be directed into the reaction mixture from different directions [FIGS. 2, 3 and 4]. In addition, the critical shape elements of the part [12 in FIG. 4] can be formed in the resin without taking the time to fully cure the resin contained inside [13 in FIG. 4] the three-dimensional surface. The "skinned" part can be removed from the resin and completely cured by heat or other source of energy.

Example 6. To minimize random polymerization in unintended zones in the reaction mixture, the ion beam(s) and reaction mixture can be reoriented in any of the Examples 1-5, so that the unavoidable linear energy transfer from the incoming ions is diluted over larger volumes of material. This technique is used in ion beam cancer therapy to minimize damage to healthy tissues. Alternatively, the reaction mixture is moved or rotated such that the ions traverse different zones of the resin en route to a same planned curing zone.

Example 7. If desired the ion beam, can operate in a mode very similar to UV-based continuous interface printing. In this case, the Bragg peak is adjusted to facilitate adhesion of the build to a movable stage and is redundantly scanned at that depth as the stage is progressively moved away from the interface. The interface could be the top surface of the resin or near any side or bottom of the container. The container would not need to be permeable to oxygen (as in CLIP). Thus, even though the ion beam is operating more or less like three-dimensional printing, it provides much more flexibility.

Figure 5:
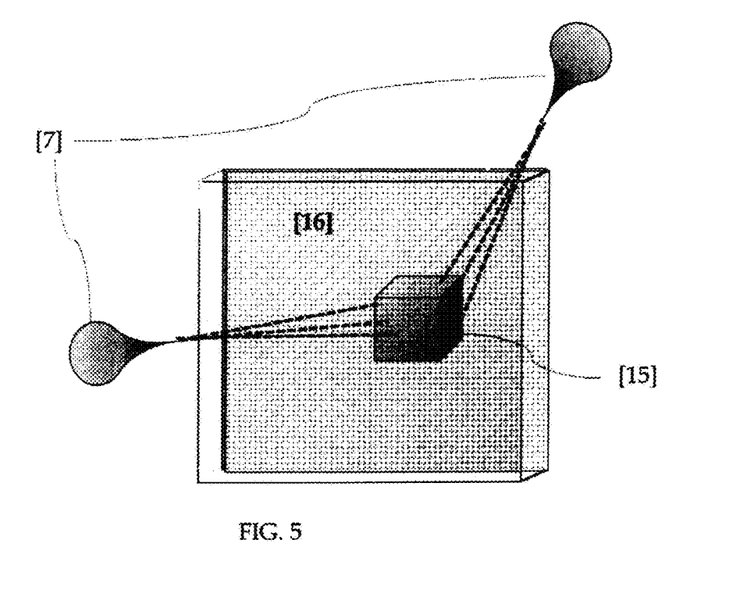
FIG. 5. This embodiment shows ion beams from two independent sources [7] building a part [15] within a matrix composed of metallic or other inert material particles (e.g. glass, plastic) [16] and a small amount of resin such that the particles are in contact and the resins is used as an adhesive.

Example 8. This embodiment is similar to Example 2 except that the particles and resin are in a ratio that brings the particles into continuous contact. In this configuration

[FIG. 5], the resin merely acts as an adhesive among the particles when it is cured. The liquid resin may be of the same material as the particles or it may be different. This configuration would allow for very fast fabrication because of the relatively small amounts of resin that actually have to be cured. The particles may be inert materials (meta: s, glass, plastic, carbon) and/or they may be fusible such that the cured part may be heated to melt the particles into a solid mass.

Example 9. As in Example 8, the filler may be metal particles (e.g., alloys of Al, Cu, Fe) and the resin is selectively cured by the ion beam to form a "skin" defining the part to be manufactured. The resin and metallic filler that is not encapsulated by the "skin" is diluted and washed away, The proto-part defined by the skin may be perforated to displace and remove the interior resin, leaving essentially only the metal particles retained inside the skin. Then the proto-part is heated (e.g., by induction heating) to fuse the metal particle together into a metal part. In some cases, it will be possible to remove the skin and encapsulated resin by heating and oxidizing or reducing the resin (e.g., to $CO_2$ or $CH_4$, which can be removed as a gas) before fusing the metal particles into a single part.

Example 10. A liquid resin might be injected into biological tissue and cured by an ion beam, e.g., to heal or replace bones or connective tissue or fill a cavity.

Example 11. An ion beam might be used as a method of initiating a chemical reaction that releases toxic products from a resin or monomer within a targeted biological system. For example, a small piece of resin might be introduced into a tumor or abscess and targeted with an ion beam causing it to breakdown and release compounds that are toxic at high concentration but biologically innocuous at low concentrations (e.g., HCl).

What is claimed is:

1. A method for manufacturing a product by initiating curing of a resin at a Bragg-peak of a controlled proton beam comprising the steps of:
   a. providing a reaction mixture, the controlled proton beam, and a temperature-controlled reaction vessel, said reaction mixture comprised of either a solid, or a liquid containing solid supports, fillers, prefabricated parts, or reinforcing materials;
   b. placing the reaction mixture into the reaction vessel;
   c. selectively sending the controlled beam of protons into the reaction mixture to create three-dimensional regions, said three-dimensional regions defined by a trace of the Bragg peak of the beam of protons in which curing of the resin occurs;
   d. removing the resin in a partially cured state from the reaction mixture, and subsequently completing the cure by heating or application of another form of energy.

2. The method of manufacturing a product as claimed in claim 1, wherein the reaction mixture is comprised of said resin, said resin being a polymer resin that can be cured by a free radical mechanism, wherein said reaction mixture contains polymerization initiators or inhibitors to facilitate controlled curing and to set a lower limit for applied energy density for triggering polymerization, crosslinking, and curing of the resin.

3. The method of manufacturing a product as claimed in claim 1 or 2, wherein the reaction mixture additionally includes inert particles that are encapsulated in the product, said inert particles thereby modifying the bulk properties of the product.

4. The method of manufacturing a product as claimed in claim 3, in which the reaction vessel is purged or pressurized to saturate the reaction mixture with a gas which acts as a polymerization inhibitor or accelerator or provides or alters properties of the product.

5. The method of manufacturing a product as claimed in claim 1, wherein the proton beam and/or the reaction mixture are moved or rotated such that the protons traverse different zones of the resin in route to a same planned curing zone as defined by traces of the Bragg peak.

6. The method of manufacturing a product as claimed in claim 1, further comprising a plurality of controlled proton beams, with said plurality of controlled proton beams including said controlled proton beam, wherein the controlled proton beams of said plurality of controlled proton beams are simultaneously applied from different directions to expedite curing.

7. The method of manufacturing a product as claimed in claim 1, wherein any other form of energy, directed or undirected, is applied to the reaction mixture concurrent with the proton beam used to facilitate formation or curing of the product.

8. The method of manufacturing a product as claimed in claim 1, wherein said reaction mixture includes prefabricated parts, wherein the prefabricated parts are positioned in the reaction mixture and are joined by curing resin between them.

9. The method of manufacturing a product as claimed in claim 1, wherein a liquid or gas is injected into the reaction mixture to form one or more bubbles within the resin before, during, or after application of the proton beam.

10. The method of manufacturing a product as claimed in claim 1, wherein a movable stage or support for the product being manufactured is introduced into the resin to act as a platform upon which the product is manufactured.

11. The method of manufacturing a product as claimed in claim 1, wherein shielding is used inside or outside the reaction vessel to assist in attenuating the proton beam without necessarily becoming an element of the product being manufactured.

12. The method of manufacturing a product as claimed in claim 1, wherein the controlled proton beam forms the product independent of a working surface.

13. A method for manufacturing a product by initiating curing of a resin at a Bragg-peak of a controlled proton beam comprising the steps of:
   a. providing a reaction mixture, the controlled proton beam, and a temperature-controlled reaction vessel, said reaction mixture comprised of a solid or a liquid;
   b. placing the reaction mixture into the reaction vessel;
   c. selectively sending the controlled beam of protons into the reaction mixture to create three-dimensional regions, said three-dimensional regions defined by a trace of the Bragg peak of the beam of protons in which curing of the resin occurs;
   d. removing the resin in a partially cured state from the reaction mixture, and subsequently completing the cure by heating or application of another form of energy, and wherein prefabricated parts or materials are added to the reaction mixture either before application of the proton beam, or concurrent with the application of the proton beam, during a pause in the application of the proton beam or after application of the proton beam, and further wherein said materials include solid supports, fillers, reinforcing materials, or inert particles, wherein said inert particles would be encapsulated in the product, said inert particles thereby modifying the bulk properties of the product.

14. The method of manufacturing a product as claimed in claim 13, wherein after application of the proton beam the cured resin acts as an adhesive among the inert particles in the reaction mixture.

15. The method of manufacturing a product as claimed in claim 14, wherein said inert particles include particles of metals or alloys that are in contact with one another with the resin filling intervening spaces among them, such that, after application of the proton beam or induction heating, the metal and resin or carbon derived from the resin form a solid part.

* * * * *